United States Patent [19]

Tanabe et al.

[11] 4,150,239

[45] Apr. 17, 1979

[54] PROCESS FOR PRODUCING 1,4-GLYCOL DIESTER

[75] Inventors: Yasuo Tanabe; Jun Toriya, both of Kurashiki, Japan

[73] Assignee: Mitsubishi Chemical Industries Ltd., Tokyo, Japan

[21] Appl. No.: 801,219

[22] Filed: May 27, 1977

[30] Foreign Application Priority Data

Jun. 2, 1976 [JP] Japan .................................. 51-64387
Jun. 2, 1976 [JP] Japan .................................. 51-64388

[51] Int. Cl.² ............................................. C07C 67/05
[52] U.S. Cl. ..................................... 560/244; 260/681
[58] Field of Search ......................... 560/244; 260/681

[56] References Cited

U.S. PATENT DOCUMENTS

| | | | |
|---|---|---|---|
| 2,204,157 | 6/1940 | Semon | 260/681 |
| 2,375,086 | 5/1945 | Davis | 260/681 |
| 2,391,509 | 12/1945 | Pines | 260/681 |
| 3,671,577 | 6/1972 | Ono | 560/244 |
| 3,755,423 | 8/1973 | Onoda | 560/244 |
| 3,872,163 | 3/1975 | Shimizu | 560/244 |
| 4,010,197 | 3/1977 | Toriya | 560/263 |
| 4,057,472 | 11/1977 | Toriya | 560/244 |

Primary Examiner—James O. Thomas, Jr.
Assistant Examiner—Michael Shippen
Attorney, Agent, or Firm—Oblon, Fisher, Spivak, McClelland & Maier

[57] ABSTRACT

A process for producing 1,4-glycol diester from unsaturated glycol diesters prepared by reacting butadiene, acetic acid and oxygen or an oxygen-containing gas in the presence of a palladium catalyst or, from saturated glycol diesters prepared by hydrogenating said unsaturated glycol diesters, wherein, 1,4-glycol diester is separated from the isomer mixture of glycol diesters prepared, the residual glycol diester isomers are decomposed by heating and butadiene and/or acetic acid produced on decomposition are recycled to the process for the production of glycol diesters.

10 Claims, No Drawings

PROCESS FOR PRODUCING 1,4-GLYCOL DIESTER

BACKGROUND OF THE INVENTION

This invention relates to a process for producing glycol diesters. It has been known so far that diacetoxybutenes can be produced by reacting 1,3-butadiene, acetic acid and oxygen or oxygen containing gas in the presence of a palladium catalyst. The diacetoxybutenes thus produced consist of a mixture of various isomers such as of 1,4-diacetoxybutene and 2,4- and 3,4-diacetoxybutenes and are required to be separated from each other since the mixture has only a restricted application as it is. Among the above isomers, 1,4-isomer is a useful substance and can be used for the production of 1,4-butene diol through hydrolysis or dihydrofuran through deacetoxy-cyclization. Alternatively, the 1,4-diacetoxybutene is further hydrogenated into 1,4-diacetoxybutane which can be used for the production of 1,4-butane diol through hydrolysis or tetrahydrofuran through deacetoxy-cyclization. While on the other hand, other isomers have less applications and most of them were only discarded with no effective utilization.

The inventors have made an earnest study on the effective utilization of the isomers other than the 1,4-isomer and, as a result, found that these isomers can be decomposed into acetic acid and butadiene on heating under specific conditions.

More specifically, the inventors have discovered that thermal decomposition of isomers other than 1,4-diacetoxybutene such as 3,4-diacetoxybutene, 1,3-diacetoxybutene and the like, as well as the corresponding diacetoxybutanes which are left after the separation of 1,4-diacetoxybutene or 1,4-diacetoxybutane can easily produce butadiene and/or acetic acid usable as the starting material and have succeeded in the development of the process for producing 1,4-diacetoxybutene or 1,4-diacetoxybutane at a high efficiency by the reuse of the resulting butadiene and/or acetic acid as the starting material for the production of diacetoxybutenes.

SUMMARY OF THE INVENTION

It is, accordingly, an object of this invention to provide a process for producing 1,4-glycol diesters such as 1,4-diacetoxybutene or 1,4-diacetoxybutane with an industrial advantage and the object can be attained by the process according to this invention which comprises reacting butadiene, acetic acid and oxygen or oxygen-containing gas in the presence of a palladium catalyst, further hydrogenating, if required, the reaction products, separating 1,4-glycol diester from the isomer mixture of glycol diesters prepared, subjecting the residual glycol diester isomers to heat treatment to decompose the glycol diesters, and recycling resulting butadiene and/or acetic acid as the part of starting materials.

The heat treatment is performed by heating the glycol diester isomers at a temperature above 300° C. or heating the isomers at a temperature below 300° C. in the presence of an acid catalyst.

DETAILED DESCRIPTION OF THE INVENTION

It is well known and various proposals have been made for the process of producing diacetoxybutenes by the reaction of butadiene, acetic acid and oxygen or oxygen-containing gas in the presence of a palladium catalyst for example U.S. Pat. No. 3,922,300, and the various known processes are applicable to this invention. Generally, butadiene, acetic acid and oxygen or oxygen-containing gas are reacted in the presence of a palladium catalyst with or without using solvent in any desired manner such as of fixed-bed type, fluidized-bed type and suspended catalyst system.

The palladium catalyst used herein includes catalysts in uniform solution phase comprising of palladium salt and redox agent such as copper salt, and solid catalysts comprising of metal palladium or metal salt thereof incorporated, as a cocatalyst, with such metals as copper, silver, zinc, nickel, chromium, iron, cobalt, cadmium, tin, lead, molybdenum, tungsten, antimony, tellurium, selenium, bismuth, alkali metals, alkaline earth metals or the like, as well as the salts thereof. Preferred catalysts are those consisting of palladium metal and, as a cocatalyst, at least one of the metals selected from the group consisting of bismuth, selenium, antimony, and tellurium supported on a catalyst carrier. The supports to be used herein include, for example, active carbon, silica gel, silica alumina, clay, bauxite, magnesia, diatomacecus earth, pumice and the like and, among all, the use of active carbon is preferred. The amount of the catalyst metal in a supported catalyst is generally selected from the range of 0.1–20% for palladium metal and 0.01–30% for other cocatalyst metal.

The reaction is conducted under a temperature usually in the range of 40°–180° C. and, preferably, 60°–150° C. under a pressure above normal pressure. Separation of water, acetic acid, high boiling components and catalyst from reaction products, for example, by way of distillation produces an isomer mixture such as 1,4-diacetoxybutene-2, 3,4-diacetoxybutene-1, 2,4-diacetoxybutene-1, 1,3-diacetoxybutene-1, 1,3-diacetoxybutene-2 and the like.

1,4-Diacetoxybutene is separated from the isomer mixture of diacetoxybutenes through an appropriate means and the residual isomers are decomposed into butadiene and acetic acid and reused as the starting material according to this invention. Isomer separation is usually conducted through distillation wherein 1,4-isomer can be obtained as bottoms and other residual isomer mixture are obtained as distillates by conducting the distillation, for example, in a distillation column having 40 theoretical plates under the conditions of a pressure in the range of 10–50 mmHg and at a reflux ratio in the range of 40–60.

The process of this invention is also applicable to diacetoxybutanes which are produced by the further hydrogenation of diacetoxybutenes. The hydrogenation is also conducted according to the known process. That is, it can be conducted by contacting the isomer mixture of diacetoxybutenes produced in the foregoing process with hydrogen in the presence of a hydrogenation catalyst. The hydrogen used herein is not necessarily be pure but may be diluted with inactive gas, unsaturated hydrocarbon or the like. The concentration of hydrogen have no particular limit and are usually more than 10% by volume, preferably, more than 50% by volume.

Hydrogen sources usable herein include those hydrogen from usual water-electrolysis and reforming, as well as gas exhausted from a reaction system, for example, the gas which results from the gas-liquid separation of reaction product.

Preferred hydrogenation catalysts include catalysts of palladium or nickel supported on a carrier. Metal palladium supported on active carbon, alumina, magnesia or the like is used, for example, as the palladium catalyst. The nickel catalysts include those supported catalysts of metal nickel such as Raney nickel, reduced nickel or the like alone or incorporated with Zn, V, Fe, Co, Ca, Ti or the like as a cocatalyst. The preferred carriers usually used herein include alumina, silica gel, silica alumina, clay, bauxite, magnesia, diatomaceous earth and pumice. Preferred hydrogenation temperatures lie in the range of 40°–180° C. and preferred pressures above normal pressure and, preferably, in the range of 10–200 kg/cm².

The hydrogenation is preferably effected in two stages in which hydrogenation is started at first at a comparatively low temperature and then completed at a high temperature. After the completion of the hydrogenation, 1,4-diacetoxybutane is separated and recovered by way of distillation or the like. In the separation of 1,4-diacetoxybutane from the hydrogenating reaction product by way of distillation, 1,4-diacetoxybutane is obtained as a bottom product and other residual components containing other diacetoxybutane isomers are obtained as distillates in the distillation, for example, under the conditions of a pressure in the range of 70–200 mmHg, preferably, 100–150 mmHg, number of theoretical plates of in the range of 10–100 and, preferably, 30–50 plates, and reflux ratio in the range of 1–10, preferably, 2–5.

Glycol diesters such as 3,4- or 2,4-diacetoxybutene or corresponding diacetoxybutanes left after the separation of 1,4-isomer are subjected to heat treatment at a temperature above 300° C. or at a temperature below 300° C. in the presence of an acid catalyst.

Liquid or solid non-volatile acids are used as acid catalysts for the heat treatment of the residual glycol diesters at a temperature below 300° C. Preferred acid catalysts specifically include, for example, sulfuric acid, phosphoric acid, paratoluenesulfonic acid, cation exchange resins and the like. Liquid non-volatile acids such as sulfuric acid, paratoluenesulfonic acid, phosphoric acid and the like are preferred among all. Heating temperature is selected from the range less than 300° C., usually, in the range of 80°–300° C. preferably, 110°–200° C. The heat treatment is also performed by only heating the residual glycol diester isomers at a temperature in the range of 300° C. to 900° C., preferably 400° C. to 900° C. and, more preferably, in the range of 550°–850° C. While the catalysts are not always necessary for the heat treatment of at above 300° C., more advantages are obtainable by the use of a catalyst which promotes the usual dehydrogenation for hydrocarbons. Such dehydrogenation catalysts include specifically solid acid catalysts such as silica alumina, silica titania, silica magnesia, alumina chromia and the like. Addition of an alkali metal, an alkaline earth metal or iron group metal as a cocatalyst to the above catalysts is further preferred. Platinum group metal catalysts carried on a support are preferred as well.

The pressure during heating is between about normal pressure and 20 kg/cm².G and, more preferably, between about normal pressure and 5 kg/cm².G. The presence of water during heating is also advantageous since it prevents side reactions such as carbon deposition. A copious amount of water is desired to prevent of carbon deposition but an excess amount thereof is undesired since it causes the water gas reaction to increase the yield of CO and $CO_2$. Consequently, the amount of water is specified as in the range of 0.1–100 mol, preferably, 1–10 mol per mol of glycol diester.

The method of heating has no particular restriction and any heating device of good heat conduction can be used. Heating can be effected by externally heating a pipe through which the reactant is passed or by contacting the reactant with heating medium previously heated and the like and the external heating for the pipe is most convenient.

Glycol diesters such as 3,4-diacetoxybutene, 2,4-diacetoxybutene or diacetoxybutanes corresponding thereto are decomposed by such a heat treatment to produce butadiene and acetic acid. In the process of this invention, acetic acid and butadiene as the decomposed products are recovered and reused in the reaction stage. While various collection processes known so far can be employed for the recovery of butadiene and/or acetic acid, it is usually most advantageous to let them be absorbed in a part of acetic acid which is to be supplied for the acetoxylation reaction and use the acetic acid containing them absorbed therein as the starting material. The absorption temperature is selected from the range between about freezing point of acetic acid and 100° C., preferably, between about the freezing point and 50° C. and the pressure therefor is selected from the range between normal pressure and 20 kg/cm².G and preferably between normal pressure and 5 kg/cm².G. The absorption is preferably conducted in two stages wherein acetic acid is quenched at about 100°–200° C. prior to the butadiene absorption and then butadiene is absorbed.

According to the process of this invention, as foregoings, it is enabled to decompose saturated or unsaturated glycol diester isomers other than 1,4-isomer, which have hitherto been discarded as of little use, into acetic acid and/or butadiene by a simple operation of subjecting the glycol diesters to a heat treatment under specified conditions and to recover them for reuse as the starting material. As the result, a significant increase can be obtained in the yield for 1,4-glycol diester.

This invention will now be described more specifically referring to examples thereof, but the invention is no way limited to the following example. Unless otherwise specified, all the percentages (%) in the examples represent percentage by weight (%w).

Example 1 (Production of unsaturated glycol diesters)

(1) Acetoxylation

A vertically mounted jacketted tubular reactor 50 mm in inside diameter and 10 m in length was charged with 7 kg of 4–6 mesh active carbon supporting thereon 2% palladium and a slight amount of tellurium and the reactor was kept at 90° C. by circulating oil heating medium through a jacket. Butadiene, acetic acid and nitrogen gas containing 5 mol% of oxygen are fed from the upper part of the reactor at the rates of 1.7 kg/h, 19.1 kg/h and 40 Nm³/h respectively under a pressure of 90 kg/cm².G. When exhausted liquid and gas were subjected to gas-liquid separation at 40° C. and thereafter reduced to normal pressure, liquid reaction products were flowed out at a rate of 20.2 kg/h from the gas-liquid separator. The above operation was continued for 104 hours to obtain 2100 kg of liquid products. The composition for diacetoxybutenes in the products were as below:

| | |
|---|---|
| 1,4-diacetoxybutene | 13.56% |
| 3,4-diacetoxybutene | 1.20% |

(2) Isomer separation

The above liquid products were introduced into a ten plate continuous rectifying column which was at first operated under normal pressure, at a column top temperature of 110° C. and with a reflux ratio of 0.1 to distill unreacted butadiene and then operated under a pressure of 85 mmHg, at a column top temperature of 60° C. and with a reflux ratio of 0.5 to distill out unreacted acetic acid. Thereafter distillation was effected in a 50 plate continuous rectifying column under a pressure of 25 mmHg, at a column top temperature of 108° C. and with a reflux ratio of 8 to obtain 46.2 kg of liquid distillates and 273.8 kg of liquid bottoms. The composition for each of the distillates and the liquid bottoms are as follows:

|  | liquid distillates | liquid bottoms |
|---|---|---|
| 1,4-diacetoxybutene | 31.0% | 98.8% |
| 3,4-diacetoxybutene | 54.7% | — |
| other components | 14.3% | 1.2% |

(3) Heat treatment

Liquid distillates containing 3,4-diacetoxybutene obtained in the above isomer separation (2) and paratoluenesulfonic acid were fed at a rate of 0.462 kg/h and 0.05 kg/h respectively from the upper part of a glass reactor of 100 mm in inside diameter and 700 mm in height under a normal pressure.

While on the other hand, steam was supplied at 0.05 kg/h from the bottom of the reactor, which was placed in an oil bath to kept at a 140° C. Unreacted reactants and paratoluenesulfonic acid were taken out from the bottom of the reactor at 0.1 kg/h. From the top of the reactor, was taken out gas phase distillate which were introduced into the bottom of an absorption column of 100 mm in inside diameter, 5,000 mm in height and packed with 12.5 mm ceramic Berl saddles. Exhausted gas was released from the top of the column and, at the same time, acetic acid was introduced therein at 30° C. and at a rate of 19.1 kg/h. The acetic acid containing gas absorbed therein (hereinafter as absorption acetic acid) was recovered from the bottom of the column.

The above operation was effected continuously for 50 hours to process 23.1 kg of foregoing liquid distillates containing the 3,4-diacetoxybutene, whereby 973 kg of absorption acetic acid was obtained by using 955 kg of acetic acid.

The absorption acetic acid had the composition containing 0.43% butadiene and 99.0% acetic acid, which means that 4.2 kg butadiene and 8.3 kg acetic acid were recovered.

(4) Recycling

Glycol diesters were produced from absorption acetic acid obtained from the heat treatment.

The acetoxylation was carried out in the same manner as in (1) except using 1.62 kg/h of butadiene and 19.3 kg/h of absorption acetic acid in place of 1.7 kg/h of butadiene and 19.1 kg/h of acetic acid previously used in the acetoxylation (1) and 1050 kg of liquid products were obtained after 50 hours of operation. The composition of diacetoxybutenes in the resulted products was follows:

| 1,4-diacetoxybutene | 13.57% |
|---|---|
| 3,4-diacetoxybutene | 1.19% |

Example 2 (Production of saturated glycol diesters)

(1) Hydrogenation 23.1 kg of liquid distillates obtained from the isomer separation (2) in Example 1 (containing 54.7% of 3,4-diacetoxybutene) was added to 132.9 kg of liquid distillates resulted through the distillation of 273.8 kg of liquid bottoms obtained from the isomer separation (2) in Example 1 (containing 98.8% of 1,4-diacetoxybutene) to prepare 156 kg of isomer mixture of diacetoxybutenes, which were then hydrogenated by using a palladium catalyst supported on active carbon. The hydrogenating reaction was conducted in two stages using two reactors. The temperature of heating medium in jackets of first reactor was at 70° C. and the second one was at 120° C. The liquid products thus obtained had the following composition:

| 1,4-diacetoxybutane | 85.8% |
|---|---|
| 3,4-diacetoxybutane | 7.9% |
| butylacetate | 2.0% |
| acetic acid | 1.1% |

(2) Isomer separation

The hydrogenated products were distilled using a 50 plate continuous rectifying column under a pressure of 30 mmHg, at a column top temperature of 110° C. and with a reflux ratio of 10 to obtain 26.0 kg of liquid distillates having the following composition and 131 kg of liquid bottom containing 99.9% of 1,4-diacetoxybutane:

| Composition of the liquid distillates | |
|---|---|
| 1,4-diacetoxybutane | 15.3% |
| 3,4-diacetoxybutane | 47.8% |
| butylacetate | 12.1% |
| acetic acid | 6.7% |

(3) Heat treatment

Liquid distillates obtained from the isomer separation (2) and sulfuric acid were fed at 0.536 kg/h and 0.05 kg/h respectively under a normal pressure from the upper part of a glass reactor of 100 mm in inside diameter and 700 mm in height, and steam was fed at 0.05 kg/h from the bottom of the reactor, which was entirely placed in an oil bath to kept at 160° C. The mixture of unreacted reactants and sulfuric acid were taken out at 0.1 kg/h from the bottom of the reactor. Gaseous distillates were taken out from the top of the reactor and introduced into the bottom of an absorption column which is 100 mm in inside diameter, 5,000 mm in height and packed with 12.5 mm ceramic Berl saddles. The exhaust gas was released from the top of the column and acetic acid at a temperature of 30° C. was introduced therein at 19.1 kg/h. Acetic acid containing gas absorbed therein was recovered from the bottom of the reactor. 26.0 kg of the liquid distillates obtained from the isomer separation (2) was thus processed. As the result, 981.8 kg of absorption acetic acid was obtained by using 955 kg of acetic acid. The absorption acetic acid had the following composition:

| Butadiene | 0.41% |
|---|---|
| Acetic acid | 98.5% |

This means that 4 kg of butadiene and 12 kg of acetic acid were recovered.

(4) Recycling

The acetoxylation was carried out in the same manner as in (1) of Example 1 except using 1.62 kg/h of butadiene and 19.4 kg/h absorption acetic acid in place of 1.7 kg/h of butadiene and 19.1 kg/h of acetic acid used in the acetoxylation process (1) of Example 1 and the acetoxylation reaction was continued for 104 hours. The resulted 2100 kg of liquid products were further subjected to rectification to obtain 320 kg of diacetoxybutenes. The composition was as below:

| | |
|---|---|
| 1,4-diacetoxybutene | 89.0% |
| 3,4-diacetoxybutene | 7.9% |

The amounts for each of the acetoxybutenes were substantially the same as those obtained without using absorption acetic acid.

Example 3 (Production of unsaturated glycol diesters)

(1) Acetoxylation

From the upper part of the reactor, which was the same reactor as used in the acetoxylation process in Example 1 and temperature of heating medium in the jacket was kept at 87° C., were fed butadiene at 1.7 kg/h, acetic acid at 19.1 kg/h and nitrogen gas containing 5 mol % oxygen at 40 Nm$^3$/h and reacted under the same reaction conditions as in the acetoxylation process in Example 1. As the result, 2100 kg of reaction products of a composition containing 13.10% of 1,4-diacetoxybutene, and 1.15% of 3,4-diacetoxybutene were produced.

(2) Isomer separation

The liquid products obtained from the above acetoxylation (1) were separated in the same apparatus and under the same conditions as used in the isomer separation (2) in Example 1 to obtain 44.3 kg of distillates and 264.5 kg of liquid bottom. They had the following composition:

| | liquid distillates | liquid bottoms |
|---|---|---|
| 1,4-diacetoxybutene | 31.0% | 98.8% |
| 3,4-diacetoxybutene | 54.7% | — |
| other components | 14.3% | 1.2% |

(3) Heat treatment

The liquid distillates obtained from the isomer separation (2) and water were introduced at 0.443 kg/h and 0.10 kg/h respectively by way of an evaporator into SUS 316 stainless steel tubular reactor of 10 mm in inside diameter and 2 m in length. The reactor was packed with 3 mm dia. silica alumina and heated electrically at 750° C. The decomposed gas discharged from the reactor was wholly cooled to 150° C. and was separated the unreacted reactants therefrom. Then, the gas was introduced to the bottom of an absorption column of 10 mm in inside diameter, 5,000 mm in height and packed with 12.5 mm ceramic Berl saddles. Acetic acid at 30° C. was introduced from the top of the column at 19.1 kg/h and contacted with the decomposed gas. Acetic acid containing the decomposed gas absorbed therein was taken out from the bottom of the column while the exhaust gas was released from the top of the column.

The above procedure was continued for 50 hours to process one-half amount of the liquid distillates obtained from the isomer separation (2). As the result, 977 kg of absorption acetic acid was obtained by using 955 kg of acetic acid. The absorption acetic acid had the following composition:

| | |
|---|---|
| Butadiene | 0.35% |
| Acetic acid | 99.5% |

This means that 3.4 kg of butadiene and 17 kg of acetic acid were recovered.

(4) Recycling

Acetoxylation was carried out in the same manner as in (1) except using 1.63 kg/h of butadiene and 19.2 kg/h absorption acetic acid in place of 1.7 kg/h of butadiene and 19.1 kg/h of acetic acid previously used in the acetoxylation (1). 2100 kg of liquid products having the following composition was obtained.

| | |
|---|---|
| 1,4-diacetoxybutene | 13.10% |
| 3,4-diacetoxybutene | 1.15% |

Example 4 (Production of saturated glycol diesters)

(1) Hydrogenation 64.2 kg, of the liquid distillates obtained from the isomer separation (2) in Example 3 was added to 128.4 kg of the liquid distillates resulted by rectifying the liquid bottoms obtained from the above process (2) to prepare 150.6 kg of mixture consisting of 1,4-diacetoxybutene and 3,4-diacetoxybutene. The isomer mixture was hydrogenated in the presence of a palladium catalyst supported on active carbon in two hydrogenation reactors at 70° C. in a first reactor and then at 120° C. in the succeeding reactor. After the operation for 50 hours, 151.5 kg of liquid products having the following composition was obtained:

| | |
|---|---|
| 1,4-diacetoxybutane | 85.8% |
| 1,2-diacetoxybutane | 7.9% |
| butylacetate | 2.0% |
| acetic acid | 1.1% |

(2) Isomer separation

The liquid products obtained from the hydrogenation process were introduced into a 50 plate continuous rectifying column which was operated under a pressure of 30 mmHg, at a column top temperature of 110° C. and with a reflux ratio of 10 to result 25.1 kg of liquid distillates containing 15.3% of 1,4-diacetoxybutane, 47.8% of 3,4-diacetoxybutane, 12.1% of butylacetate and 6.7% of acetic acid, and 126.4 kg of liquid bottoms containing 99.9% of 1,4-diacetoxybutane.

(3) Heat treatment

The above liquid distillates and water were introduced at 0.502 kg/h and 0.10 kg/h respectively through an evaporator into a SUS 316 stainless steel tubular reactor of 6 mm in inside diameter and 10 m in length and kept at 800° C. The entire portion of the discharged decomposition gas was cooled to 150° C. and separated unreacted solution therefrom. Then the decomposed gas was introduced to the bottom of an absorption column of 100 mm in inside diameter, 5,000 mm in height and packed with 12.5 mm ceramic Berl saddles. Acetic acid at 30° C. was introduced at 19.1 kg/h from the top of the column and acetic acid containing the decomposed gas absorbed therein was taken out from the bottom of the column. 25.1 kg of the liquid distillates were treated through the above procedure during 50 hours. 967 kg of absorption acetic acid was obtained by using 955 kg of acetic acid. The composition of the absorption acetic acid was as follows:

| | |
|---|---|
| Butadiene | 0.32% |
| Acetic acid | 99.4% |

This means that 3.1 kg of butadiene and 6.2 kg of acetic acid were recovered.

(4) Recycling

Acetoxylation was carried out in the same manner as in Example 1 except using butadiene at 1.64 kg/h and absorption acetic acid at 19.2 kg/h in place of butadiene at 1.7 kg/h and acetic acid at 19.1 kg/h previously used therein and they were subjected to the same operation for 104 hours as in Example 3 to obtain 2100 kg of reaction product. The diacetoxy butenes had the following composition:

| | |
|---|---|
| 1,4-diacetoxybutene | 13.10% |
| 3,4-diacetoxybutene | 1.15% |

What is claimed is:

1. A process for producing 1,4-glycol diesters, which comprises:

forming a mixture of $C_4$ glycol diesters by reacting butadiene and acetic acid in the presence of oxygen or an oxygen-containing gas over a palladium catalyst;

separating said mixture into two fractions one of which essentially contains 1,4-$C_4$ glycol diester and the other of which essentially contains all of the $C_4$ glycol diesters produced in said reaction other than the 1,4 isomer;

thermally decomposing said fraction containing $C_4$ glycol diesters other than the 1,4 isomer in the presence of water to acetic acid and butadiene; and recycling the resulting butadiene and acetic acid to said reaction as a portion of the starting materials.

2. The process of claim 1, wherein said fraction is thermally decomposed at a temperature in the range of 80° C. to 300° C. in the presence of an acid catalyst.

3. The process of claim 2, wherein the amount of said water is in the range of 0.1-100 moles per mole of glycol diesters.

4. The process of claim 2, wherein said temperature lies in the range of 110° C. to 200° C.

5. The process of claim 2, wherein the catalyst is an acid selected from the group consisting of paratoluenesulfonic acid, sulfuric acid and phosphoric acid.

6. The process of claim 1, wherein said fraction is thermally decomposed at a temperature in the range of 300° C. to 900° C.

7. The process of claim 6, wherein the amount of said water is in the range of 0.1-100 moles per mole of glycol diesters.

8. The process of claim 6, wherein said temperature is higher than 400° C.

9. The process of claim 6, wherein said fraction is thermally decomposed in the presence of a solid acid catalyst selected from the group consisting of silica-alumina, silica-titania, silica-magnesia, and alumina-chromia.

10. The process of claim 1, which further comprises: hydrogenating said mixture of diesters before separating said mixture into two fractions.

* * * * *